United States Patent [19]

Takacs et al.

[11] 4,276,701

[45] Jul. 7, 1981

[54] APPARATUS FOR THE DRYING OF WET, PASTY AND/OR FUSIBLE MATERIALS

[75] Inventors: István Takács; Péter Rudolf; Béla Szabó; György Kerey, all of Budapest, Hungary

[73] Assignee: Richter Gedeon Vegyészeti Gyár RT, Budapest, Hungary

[21] Appl. No.: 97,969

[22] Filed: Nov. 28, 1979

[30] Foreign Application Priority Data

Mar. 21, 1979 [HU] Hungary .................. RI 701

[51] Int. Cl.³ .................................. F26B 17/20
[52] U.S. Cl. ........................... 34/109; 34/179; 34/182; 34/183; 432/239; 366/295; 366/316; 366/317; 241/38; 241/45; 241/278 R; 241/296
[58] Field of Search ............... 34/181, 182, 183, 109, 34/179; 366/286, 295, 315, 316, 317; 432/121, 139, 144, 151, 239; 241/38, 45, 278 R, 296

[56] References Cited

U.S. PATENT DOCUMENTS

| | | | |
|---|---|---|---|
| 780,926 | 1/1905 | Welds | 366/286 |
| 1,727,753 | 9/1929 | De Bethune | 366/316 |
| 2,470,315 | 5/1949 | McGehee | 34/109 |
| 3,062,627 | 11/1962 | Zuiderweg | 366/316 |
| 3,351,434 | 11/1967 | Grimes et al. | 366/316 |
| 3,377,139 | 4/1968 | MacGregor et al. | 366/316 |
| 3,481,049 | 12/1969 | Heacock et al. | 34/109 |

FOREIGN PATENT DOCUMENTS

| | | |
|---|---|---|
| 1174072 | 8/1969 | United Kingdom . |
| 1313126 | 4/1973 | United Kingdom . |
| 1445856 | 8/1976 | United Kingdom . |
| 1522969 | 8/1978 | United Kingdom . |

*Primary Examiner*—Larry I. Schwartz
*Attorney, Agent, or Firm*—Karl F. Ross

[57] ABSTRACT

A drier, especially for viscous materials, comprises a double-wall cylindrical vessel which is heated and to which the material to be dried is fed at one end with the dried material being removed at the opposite end. A drying gas inlet is connected to the drying chamber to pass the drying gas in counterflow or uniflow with the material and a shaft is rotatable along the axis of the chamber and carries adjustable disks with alternately inner and outer openings so that the material path through the vessel is deflected toward and away from the axis as the material passes successively through adjustable-length cells between these disks. All of the disks carry blades which scrape the material from the heated wall from the vessel and at least some of the disks carry rollers of predetermined spacing from this wall to adjust the particle size of the dried product.

8 Claims, 6 Drawing Figures

APPARATUS FOR THE DRYING OF WET, PASTY AND/OR FUSIBLE MATERIALS

FIELD OF THE INVENTION

The invention relates to apparatus for the drying of wet, pasty and/or fusible materials, especially non-fluidizable, greasy, sticky, pulpy materials, sludges, fragmentary organ scraps and similar substances derived from slaughterhouses.

BACKGROUND OF THE INVENTION

For drying of the pasty, pulpy material of high moisture content, or those of other similar consistency, various types of driers are used which—depending on the method of heat transfer—fall into two main groups: the contact or indirect and the convective or direct heat transfer system. Recently with the combination of these two systems the so-called contact-convective drier has been developed.

In driers of the contact (indirect) system the material to be dried receives the heat necessary for evaporation of the moisture through heat conduction from the wet surface in contact with it.

One of the most familiar contact driers is the single or multi-cylindrical drier for continuous operation. The internally steam heated hollow cylinder is slowly rotated in a frame construction, the material to be dried is carried in a thin layer onto the external surface with a train of rolls and the dried material is removed from the surface by a blade. In order to increase the drying capacity air is blown onto the cylinder mantle from the outside.

Another generally known type of contact drier is the heated walled mixing drier for intermittent operation. It has a vertical cylindrical which is drum externally heated and the material to be dried is carried into the interior and moved by a rotary scraper-mixer along the internal surface of the mantle, the heat transmitting surface being constantly cleaned by the scraper. The vapors arising during the process of drying are removed vacuum exhaustion or with cold air flow from the equipment.

In another familiar contact drier, bags are mounted on a hollow shaft arranged in a horizontal trough. The bags are internally and the trough externally heated with steam. The material to be dried is located in the space between the rotary bags and is loosened by blades mounted on the bags. In order to avoid simultaneous rotation, vertical blades extend between the bags ("Rotadisc" system).

For meat-meal production in animal-protein processing plants a heated screw drier is used. This drier has a double drum with heated rotary casing pipe in the interior provided with a deflecting spiral. The material to be dried passes forwardly through the annular space which is heated on both sides with the aid of the deflecting spiral rotating together with the casing pipe. The developed vapor passes through the holes of the narrow threads of the spiral casing into one or more vapor condensers mounted on the drier body.

Contact driers are of simple construction and safe operation; their heat utilization is favorable, but their applicability extends only to a narrow range of materials to be dried. On the other hand construction of the contact driers developed for drying of the materials of special consistency, e.g. pasty materials is complicated, and the operation is cumbersome. The constant renewal of the drying surface in the heated-wall mixing driers, the difficult cleaning of the interior and the high energy requirement of the mixing process cause serious problems. The high investment and operation costs represent additional disadvantages.

The material to be dried is in direct contact with the drying agent in the driers of the convective heat transfer.

One of the most familiar types of such systems is the continuous operation spray drier, in which the pulpy or pasty material is atomized to tiny drops and subjected to the effect of hot gas flow (possibly a flue gas). The drier has a large drying chamber. Atomization of the medium to be dried is mechanical, pneumatic or hydraulic. In case of necessity—since atomization of too dense material is energy- and cost-intensive, the material is made deliquescent with dispersing agents, which however are disadvantageous especially when cleanliness of the dried end product is essential. The dense material is carried into the atomizer with a screw feeder.

Fluidization driers are also known in which a stationary or moving charge is used (e.g. ceramic, glass beads, synthetic granulations) consisting of grains exceeding the grain size of the material to be dried and the fluidization drying of the pasty material or suspension takes place in the interspace or on the surface of the grains of the charge (drying of circulated layer). The grains can be created from the material to be dried. The dried product can be separated in cyclone.

The rotary drum drier (Roto-Louvre-type) was developed for the drying of non-fluidizable materials, in which the material passes from the input to the output by rotation of a drum. The mantle of the drum is "slotted" and the drying agent enters the drum tangentially and flows through the material.

A so-called swirl impulse drier fluidizes the material with air impulses ("Jet-stream"-type). The drying gas enters the vertical drum through the jet slots tangentially, agitating the material to be dried at high speed.

Disadvantages of convective type driers include unfavorable heat utilization, and energy-intensive spraying. The feed of the pasty material and operation of the sprayer are cumbersome; a large drying chamber volume is required and thus both the investment and operating costs are excessive. The charge used in the fluidization driers of the circulated-layer type increases the resistance to flow of the drying agent considerably. Consequently the use of a blower involves investment and operating cost-increasing factors.

Recently such driers have become known in which the contact and convective methods of heat transfer are combined in that the major part of the moisture is removed with convective drying in the first phase of the drying process, while the heat necessary for completion of the drying is transmitted by convective method. One of the most familiar types of driers operating on this principle is the so-called "Combined" drier developed with the combination of driers. Such driers include the cylinder belt driers and cylinder plate driers. The cylindrical drier mantle is of shaped-grooved construction. The pasty material dries during rotation of the cylinder, it develops a crusty layer which is removed with a shaped knife reaching into the grooves in the form of a comb. The so-obtained strips of material can be fed onto the after-drying belt or rotary disc.

The so-called "Devi"-type drier also uses the combined system and has a drying body of which is of cradle shape, duplicated, while the rotary shaft in the interior is fitted with a multi-threaded spiral. The drying agent is blown in at the lower part of the cradle. The mixer cuts up the encrusted material at a continuous rate and the material becomes fluidizable by the end of the first phase of the drying process. The further drying takes place in the fluidized condition of the material; the fluidizing agent is the drying agent admitted at the lower part of the cradle (e.g. hot air).

The above described combined (complex) apparatuses have been developed for the drying of certain materials of special consistency. They are generally much more complicated than driers of purely contact or convective type, and their investment and operating costs are also fairly high.

OBJECTS OF THE INVENTION

An object of the invention is to provide a drying apparatus in which materials of significantly different consistency and/or of significantly different physical and/or chemical properties—especially pasty, sticky, non-fluidizable materials of high moisture content—can be dried rationally and with a quality satisfying every requirement. A further object of the invention is to produce the dried material with a required particle size distribution (grain size).

SUMMARY OF THE INVENTION

The invention is based on the following recognition:

If in addition to the contact heat transfer hot drying gas is passed through the moving material to be dried, and convective heat transfer is used, the drying efficiency can be substantially increased. The efficiency of the drying is increased when the residence time of the material in the drying space is extended. This can be attained by dividing the cylindrical drying space into cells, in the cross sectional walls of which orifices are formed in order to ensure passage of the material to be dried and that of the drying agent. The path of movement of the media in contact with each other and effectiveness of the contact are considerably increased if the annular orifices in the consecutive cell walls are developed in the intermediate or peripheral regions. If scraper-mixer blades are mounted on the rotary cell-cross walls in the circumferential range, which rotate at a short distance from the vertical cylindrical side wall, the contact heat transfer surfaces can be continuously renewed and material sticking to the cylindrical wall of the cells can be dispersed into the deflecting gas flow, whereby effectiveness of the contacting phases and heat transfer can be considerably increased. The drying power can be intensified and drying of the materials of various consistency can be accomplished in the same unit. Finally if freely revolving rollers are mounted in part of the circumferential region of the cross directional cell walls—suitably in every second cell wall—fitting the cylindrical internal wall of the cells with certain spacing, then grain size of the end product or the grain distribution can be set according to requirements. If gaseous drying agent is passed through the equipment in quantities regulated simultaneously in uni- and counter flow, part of the dry material may be returned into the region of the wet material and thereby the effective mixing of the dry and wet material, as well as the effective drying can be further improved.

On the basis of this recognition the object of the invention are attained with a drying apparatus which has a horizontally arranged cylindrical drying space formed in the interior of the externally heated body with a mixer within it. Devices are provided for admission of the wet material and gaseous drying agent into the drying space, as well as for removal of the dried material and drying agent from the drying space. According to the invention drying space is divided into cells with spaced cross sectional (transverse) walls—suitably perpendicular to the geometrical symmetry axis—provided with orifices arranged crosswise to the geometrical symmetry axis for passing the material and the drying agent.

The transverse walls and the cylindrical side wall surrounding the drying space are rotatable relative to each other and scraper-mixer blades are fixed on the transverse wall and lie along the inner mantle surface of the side wall within the circumferential region, while the device feeding in the wet material is connected with the drying space in the region of one of its ends, and the device discharging the dried material is connected in the region of its other end.

According to a further feature of the invention, the orifices in the transverse walls are arranged alternately in the intermediate and circumferential regions of the successive walls. The transverse wall can thus be alternately reducing rings and reducing discs, with an orifice formed in the middle of each reducing ring and the reducing ring is provided with several, suitably four arms at 90° to each other extending from a centrally arranged plate toward the inner mantle surface of the cylindrical side wall and ending at a spacing from it. The transverse walls are mounted on shaft extending along the geometrical symmetry axis of the drying space, and are adjustable in longitudinal direction and thereby in a way suitable for varying the length of the cells.

Adjustment of the grain size of the dried material is made possible by the arrangement according to the invention in that freely revolving crushing rollers are mounted in the circumferential region—at least in part—of the transverse walls with a spacing from the inner mantle surface of the cylindrical side wall and this mantle surface is parallel with that of the crushing rollers.

According to a further feature of the invention, the cylinder enclosing the drying space is closed with fixed end plates on each end, and the rotatable shaft passes through the end plates, suitably with stuffing boxes and is connected with the drive.

The apparatus, with respect to the movement of the material to be dried and the gaseous agent in the drying space can be operated in purely uniflow or purely counterflow modes. For the best drying efficiency and for complicated drying tasks the apparatus is developed for mixed flow, i.e. partly uni- and partly counterflow such that the drying space has a uniflow section and a counterflow section. The former serves as the input of the drying space for the wet material, while the latter is formed in the part toward the device discharging the dried material. A gas inlet orifice is provided in the region of both ends of the drying space, in the vicinity of the end plates and a gas outlet orifice leads out of the drying space, upwardly between the uniflow and counterflow sections. In this case the pipe stub is connected to the gas outlet orifice to which a suitably cylindrical housing is attached, in which the dust filter bag connected to the pipe stub is suspended and a pipe stub leads out of the upper part of the housing outside the dust filter bag.

Separately regulated heaters, e.g. calorifiers, are built into the gaseous drying agent pipes connected separately to the uniflow and counterflow sections, and that the cylindrical wall surrounding the drying space is duplicated separately in the uniflow section and counterflow section for the purpose of regulating the contact heat transfer of these sections independently from each other, i.e. closed spaces are provided separately from each other along the outer mantle surface of the cylindrical wall, into which heaters containing separately regulated closing devices, e.g. steam pipe is connected.

SPECIFIC DESCRIPTION

Figure 1:
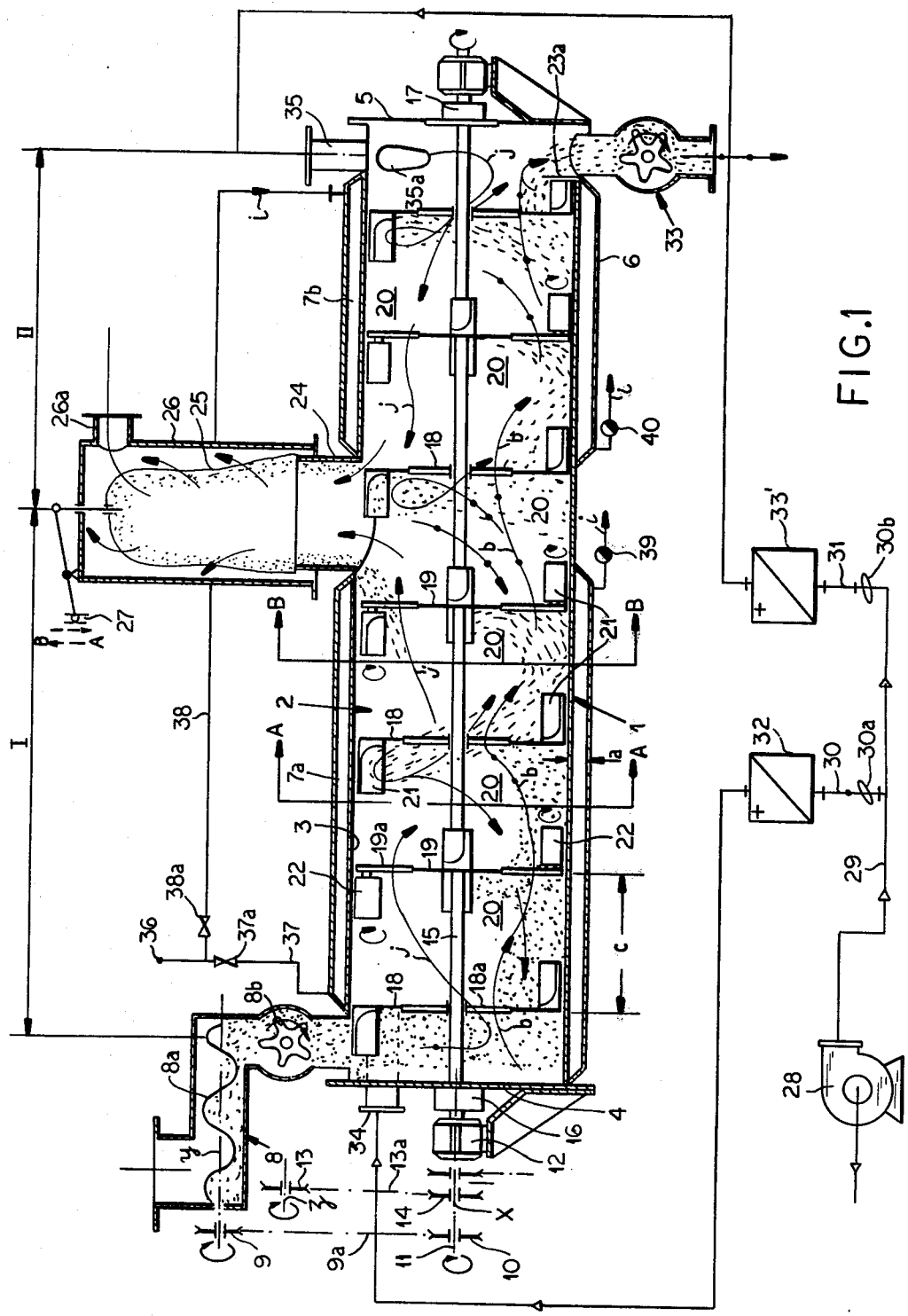
FIG. 1 is a schematic diagrammatic vertical longitudinal section through the apparatus.

Cylinder 1 is horizontal, fixed in this position, and its geometrical longitudinal axis X is horizontal. The cylinder 1 includes the drying space 2 surrounded by side wall 3 and end plates 4,5 forming the mantle of the cylinder. The drying space 2 has a uniflow section I and counterflow section II. Along these the side wall 3 of the cylinder is duplicated, i.e. surrounded by mantle 6 with spacing a from the outside, thereby forming the closed spaces 7a, 7b of annular cross section with wall 3, into which closed spaces a heating agent is admitted (see later).

For input of the material to be dried a feeder device 8 is used which comprises screw feeder 8a and cell feeder 8b connected to it and underneath it, the latter feeder leading into the cylinder 1 at its left hand end from the top. Both the screw and cell feeders are of gastight construction. The screw shaft y is driven by sprocket 9 which is connected with sprocket 10 through chain 9a. The sprocket 10 is fixed on shaft 11, driven by the drive 12. The shaft z of cell feeder 8b is driven by the sprocket 13 with the aid of chain 13a, passing over chain wheel 14 fixed to shaft 11.

Shaft 15 runs through the cylinder 1 along the horizontal geometrical longitudinal axis X of the cylinder, and is connected to the drive 12 with the use of stuffing box 16 and bearings 17 arranged outside of the drying space 2. The bearings are supported by brackets welded to the end plate 4, for example. The other end of shaft 15—on right hand side in FIG. 1—is carried in a bearing 17 similarly. The reducing rings 18 and reducing discs 19 are in rigid connection and rotable with the shaft 15 spaced at distance c from each other, dividing the drying space 2 in longitudinal direction of the cylinder 1 to cells 20. In the circumferential region of the reducing rings 18 and reducing discs 19 the mobile scraper-mixer blades 21 are fitted along the inner mantle surface of the cylindrical side wall 3, in its immediate vicinity at a distance of a few millimeters therefrom, while the crushing rollers 22 are fitted in the circumferential range of the reducing disc 19; these latter ones also move along the inner mantle surface of the cylindrical side wall 3. Flow of the material from one cell 20 to the next one is realized by the orifices 18a formed in the reducing rings 18, and by the orifices 19a formed in the reducing discs 19 (see FIGS. 2 and 3).

For carrying off the large grain size fraction forming the major part of the dried material, a gas-tight cell feeder 33 is connected to the right hand side end of cylinder 1, i.e. opposite the wet material inlet orifice, leading out of the lower part of the cylinder. Above the feeder 33 on the side opposite the end plate 5, a circular segment shaped baffle plate 23a is fixed to the side wall 3, the upper flange of which is about ¼-1/5th of the inside diameter (FIG. 3) of the cylinder. Pipe stub 24 extends upward out of the upper part of cylinder 1 in the range between the uniflow section I and counterflow section II of the drying space 2, closed by the cylindrical housing 26. The dust filter bag 25 is located in the housing 26, fitted to the pipe stub 24 at the bottom, and suspended with a mechanical vibrator 27 at the top. The pipe stub 26a leads out of the upper part of house 26 in a lateral direction.

For admission of the drying air the apparatus is provided with the ventilator 28 passing the intake air through pipe 29 into the branch-pipes 30, 31. The calorifiers 32, 33' are built into these branch-pipes—and in the direction of the air flow—valves 30a, 30b are inserted into the branch-pipes for regulation of the air volume. The branch pipe 30 is connected to pipe stub 34 and branch pipe 31 to pipe stub 35; these lead tangentially into the drying space 2 at the left hand side or at the right hand side of the cylinder 1. The inlet orifices are marked with reference numbers 34a and 35a respectively.

Side wall 3 of cylinder 1 is separately duplicated in the range of sections I and II, and the closed spaces 7a and 7b are heated from the steam network 36. The steam pipe 37 is leads into the closed space 7a along the mantle pertaining to the uniflow section I, while the steam pipe 38 is leading into the closed space pertaining to the counterflow section II, these are fitted with regulators 37a and 38a for control of the heat quantity carried into the drying space. For removal of the condensed liquid of the closed spaces 7a, 7b the condensate separators 39, 40 are provided.

Figure 2:
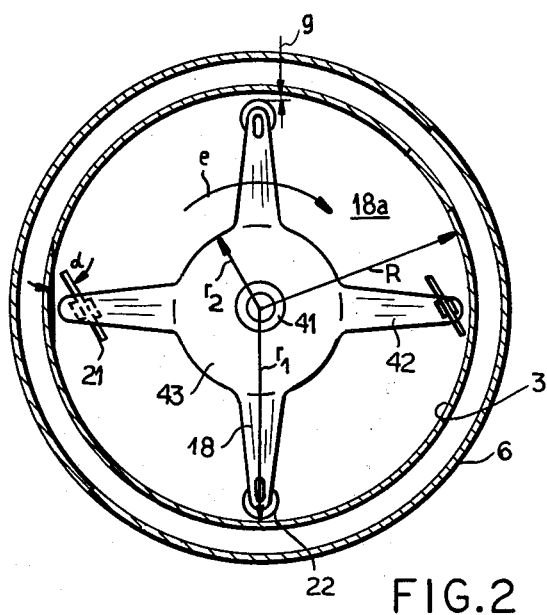
FIG. 2 is a section showing a reducing ring and taken along line A—A in FIG. 1 but drawn to a larger scale.

Construction of the reducing ring 18 can be seen from FIG. 2. The outside radius $r_1$ of the reducing ring 18 is less by spacing d, than the radius R of the cylindrical side wall 3. The inside radius of the reducing ring is marked with reference letter $r_2$. The orifice 18a of radius $r_2$ (hatched for the sake of lucidity) is broken only by the ribs 42 which connect the annular plate 43 with the hub 41, which in turn is fixed to shaft 15. The material to be dried and the drying agent flow through this orifice 18a, through the so-called "free cross section" (in uniflow and) or counterflow). In the outer circumferential region of the annular plate 43 scraper-mixer blades 21 are mounted at two places opposite each other (suitably spaced at 180°), which moving along the inner mantle surface of the cylindrical side wall 3 remove the deposited material at a continuous rate. The scraper-mixer blades 21 are at an angle α—opening toward the direction of rotation marked with arrow e, i.e. at reclining angle in relation to the direction of rotation,—to the contact plane f laid to the cylindrical house 3 at the spot where the scraper-mixer blades 21 contact the cylindrical wall. α is suitably an acute angle.

Figure 3:
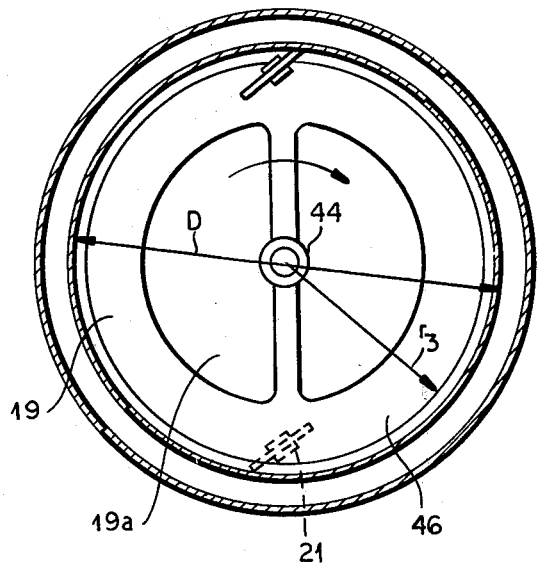
FIG. 3 is a section showing a reducing disc and taken along line B—B in FIG. 1 but drawn to a larger scale.

FIG. 3 shows the construction of a reducing disc 19 in detail to a large scale. The hub 44 keyed on the shaft 15 is fixed to the circular plate 46 of radius $r_3$.

Figure 4:
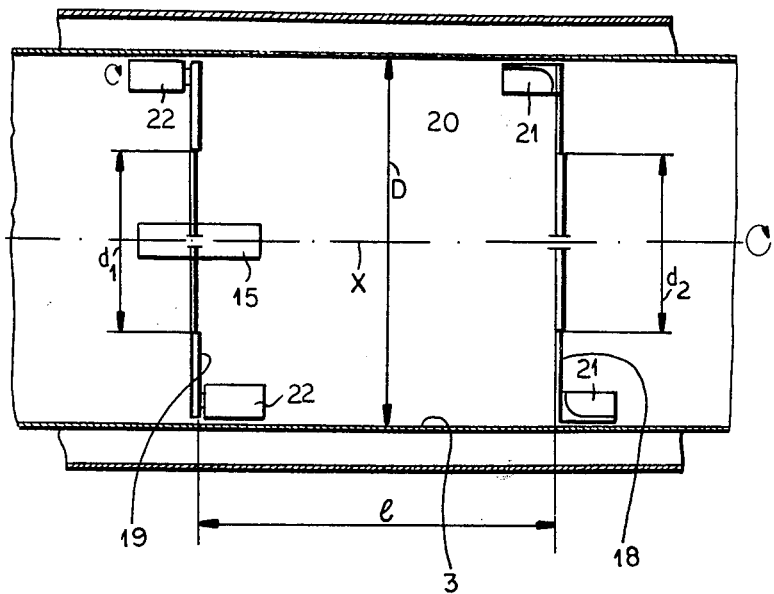
FIG. 4 is a section showing a cell surrounded by the reducing ring on one side, and by reducing disc on the other side, as in FIG. 1 but shown in a larger scale.

The vertical section of a cell 20 is shown in FIG. 4 in a larger scale than in FIG. 1., surrounded by the cylindrical side wall 3 on the side and by the reducing disc 19 and reducing ring 18 on each end. Length of the cell 20 is l, diameter D (D=2R, see designations of FIGS. 2 and 3).

Figure 5:
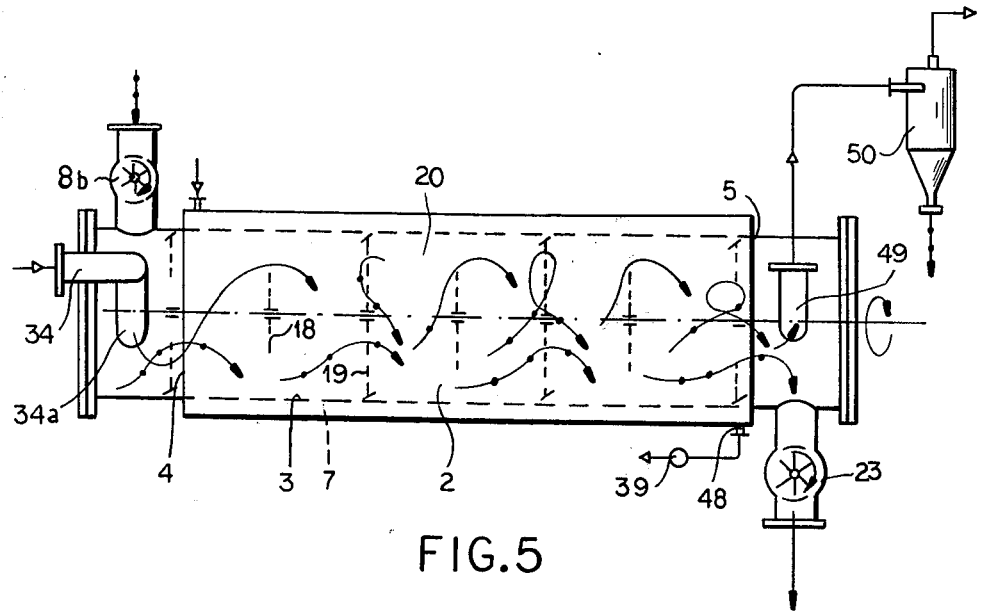
FIG. 5 is a diagrammatic vertical longitudinal section of a uniflow apparatus according to the invention.

In FIG. 5a simpler apparatus is shown for purely uniflow operation and flow of the material to be dried and the drying agent. The drying space 2 which is surrounded by side wall 3 and end plates 4,5, is divided into cells 20 by the reducing discs 19 and reducing rings 18. The agent heating the side wall 3 is admitted into the closed space 7 through pipe stub 47, while the condensate passes through pipe stub 48 into the condensate separator 39. For admittance of the drying agent the pipe stub 34 and inlet orifice 34a are provided; the material to be dried is fed in with cell feeder 8b. The dried material is discharged with the cell feeder 23 and its fine fraction through pipe 49 into the cyclone 50.

Figure 6:
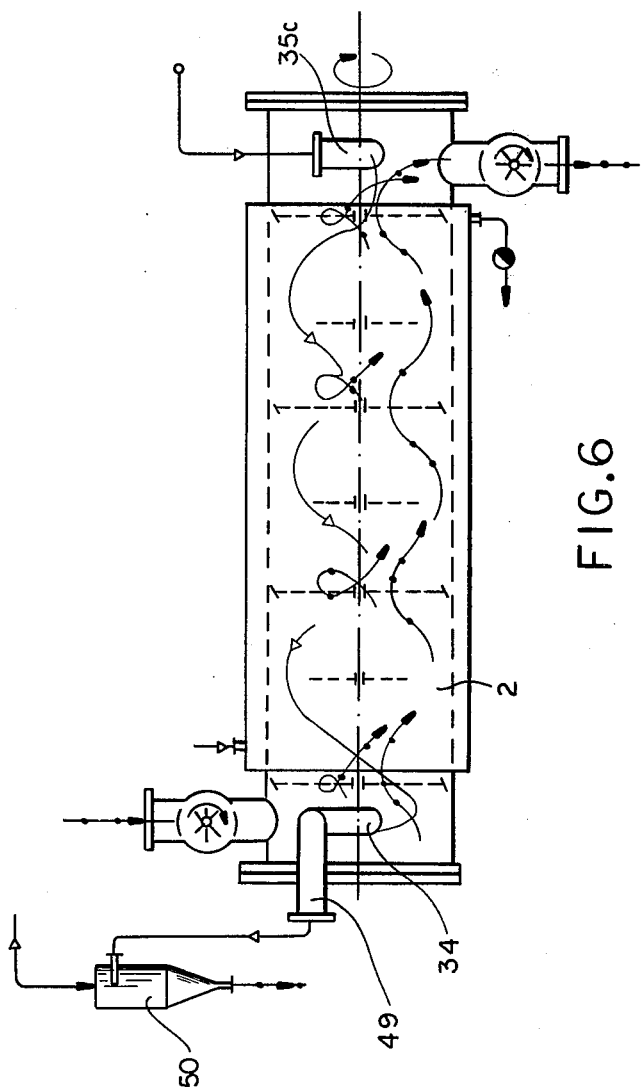
FIG. 6 is a diagrammatic longitudinal section of a counterflow apparatus according to the invention.

The apparatus shown in FIG. 6 is a counterflow system with respect to the movement of the material to be dried and the drying agent. This equipment is different from the one shown in FIG. 5 insofar that the drying agent is admitted into the drying space 2 through the inlet orifice 35c at the right hand side end of the equipment, it passes out through the outlet orifice 34 and through the pipe 49 into the cyclone 50, which is located at the inlet end of the equipment.

The wet material to be dried is carried into the feeder device 8 from the direction of the dotted arrow b, and the path of movement of the material is represented with such dotted arrows b. The direction of the steam flow ensuring the heating of the side wall 3 is indicated by arrows i (drawn on the steam pipes), while flow of the drying agent, here the hot air, is illustrated by arrows j shown with dashed line. The wet material falling into the drying space 2 from the feeder device 8 is forwarded, lifted and dropped by the scraper-mixer blades 21, while the material is heated and the moisture evaporates partly as a result of the conductive heat transfer through the side wall 3 heated from the closed spaces 7a, 7b, and partly through convective heat transfer as a result of contact with the hot air flow. The necessary residence time of the material to be dried and its proper mixing in the drying space, as well as its effective contact with the hot air are ensured with alternately arranged rotary reducing rings 18 and reducing discs 19, which force the material and hot air in varying flow directions from one cell 20 into the next one. With proper selection of the number of rollers 22, distribution and distance g (FIG. 2) measured from the cylinder mantle grain size of the dry material can be set according to the existing requirements.

What we claim is:

1. An apparatus for the drying of material, especially wet, pasty and/or fusible substances, comprising:

an axially elongated thermally conductive cylindrical wall defining a cylindrical drying space having a substantially horizontal axis;

means forming at least one annular heating chamber along the exterior of said wall;

means for passing a heating fluid through said heating chamber to heat said wall;

a pair of end walls dispoed at opposite axial ends of said space and closing same;

feeder means for introducing material to be dried into said space at one end thereof adjacent a respective end wall;

discharge means connected to said space at an opposite end thereof adjacent the other end wall for discharging dry material from said space;

inlet means communicating with said space at least at one of said ends thereof for introducing a hot drying fluid into said space for direct contact with the material therein;

outlet means connected to said space at a location axially separated from said inlet means for discharging said drying fluid from said space;

a shaft extending along said axis and journaled for rotation relative to said walls;

drive means connected with said shaft for rotating same;

a plurality of first disks mounted on said shaft and lying in respective planes transverse to said axis, said first disks comprising outwardly extending arms reaching toward said wall and defining openings located relatively outwardly from said axis;

a plurality of second disks mounted on said shaft and alternating with said first disks axially therealong whereby each first disk and a second disk axially spaced therefrom define a respective drying cell of adjustable axial length, said second disks being formed with openings communicating between said cells and located relatively inwardly with respect to said axis;

respective blades mounted on outer portions of said disks and positioned to scrape material from said wall and mix said material with said drying fluid as said material passes through said openings in said disks from cell to cell from said feeder means to said discharge means; and respective rollers journaled on outer portions of at least some of said disks and having a predetermined spacing from said wall for comminuting material drying in said space to a predetermined particle size.

2. The apparatus defined in claim 1 wherein two such blades are provided on two diametrically opposite arms of said first disks and two such rollers are provided on another two diametrically opposite arms of said first disks.

3. The apparatus defined in claim 1 wherein said blades are inclined at an acute angle to the tangent to said wall in the direction of rotation of said disks by said shafts.

4. The apparatus defined in claim 1 wherein said feeder means includes a rotary cell feeder and said discharge means includes a rotary cell dispenser.

5. The apparatus defined in claim 4 wherein said rotary cell feeder is connected to a screw feeder which advances said material to said rotary cell feeder.

6. The apparatus defined in claim 23 wherein said outlet means is provided at a location intermediate said ends and each of said ends is provided with an inlet for said drying fluid, said inlets constituting said inlet means whereby said material and said drying fluid pass in uniflow through a first portion of said space and in counterflow through the remainder thereof.

7. The apparatus defined in claim 1 wherein said inlet means is provided at the end of said space at which discharge means is disposed and said outlet means is provided at the end of said space at which said feeder means is disposed whereby said material and said drying fluid are passed in counterflow through said space.

8. The apparatus defined in claim 1 wherein said inlet means is provided at said one end of said space and said outlet means is provided at said other end of said space whereby said material and said drying fluid are passed in uniflow through said space.

* * * * *